(12) United States Patent
Rüdenauer et al.

(10) Patent No.: US 9,994,540 B2
(45) Date of Patent: *Jun. 12, 2018

(54) PRODUCTION OF 2-SUBSTITUTED 4-METHYL-TETRAHYDROPYRANS FROM STARTING MATERIALS CONTAINING 2-ALKYL-4,4-DIMETHYL-1,3-DIOXANES

(71) Applicant: BASF SE, Ludwigshafen (DE)

(72) Inventors: Stefan Rüdenauer, Weinheim (DE); Timon Stork, Bürstadt Bobstadt (DE)

(73) Assignee: BASF SE (DE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/304,283

(22) PCT Filed: Apr. 8, 2015

(86) PCT No.: PCT/EP2015/057580
§ 371 (c)(1),
(2) Date: Oct. 14, 2016

(87) PCT Pub. No.: WO2015/158584
PCT Pub. Date: Oct. 22, 2015

(65) Prior Publication Data
US 2017/0037020 A1     Feb. 9, 2017

(30) Foreign Application Priority Data

Apr. 14, 2014 (EP) ..................... 14164580

(51) Int. Cl.
*C07D 309/04* (2006.01)
(52) U.S. Cl.
CPC ................... *C07D 309/04* (2013.01)
(58) Field of Classification Search
CPC .................................. C07D 309/04
USPC ....................................... 549/356
See application file for complete search history.

(56) References Cited

U.S. PATENT DOCUMENTS

| | | | |
|---|---|---|---|
| 2,471,134 A | 5/1949 | Wright | |
| 8,546,591 B2 | 10/2013 | Koenigsmann et al. | |
| 8,618,315 B2 | 12/2013 | Gralla et al. | |
| 9,139,549 B2 * | 9/2015 | Stork | C07D 309/10 |
| 2011/0306779 A1 | 12/2011 | Gralla et al. | |
| 2014/0107352 A1 | 4/2014 | Stork et al. | |
| 2014/0163117 A1 | 6/2014 | Rudenauer et al. | |
| 2014/0213494 A1 | 7/2014 | Rudenauer et al. | |
| 2016/0060238 A1 | 3/2016 | Stork et al. | |
| 2016/0068500 A1 | 3/2016 | Stork et al. | |
| 2017/0037021 A1 * | 2/2017 | Stork | C07D 309/10 |
| 2017/0037022 A1 * | 2/2017 | Stork | C07D 309/10 |

FOREIGN PATENT DOCUMENTS

| | | |
|---|---|---|
| EP | 0122367 A2 | 10/1984 |
| EP | 0770670 A2 | 5/1997 |
| EP | 1493737 A1 | 1/2005 |
| EP | 13165767.8 | 4/2013 |
| EP | 13165778.5 | 4/2013 |
| EP | 2991973 A1 | 3/2016 |
| SU | 19752312401 | 12/1975 |
| SU | 573483 A1 | 9/1977 |
| WO | WO-2009077550 A1 | 6/2009 |
| WO | WO-2010133473 A1 | 11/2010 |
| WO | WO-2011147919 A1 | 12/2011 |
| WO | WO-2011154330 A1 | 12/2011 |
| WO | WO-2014060345 A1 | 4/2014 |
| WO | WO-2014177484 A1 | 11/2014 |

OTHER PUBLICATIONS

Gevorkyan; Armyanskii Khimicheskii Zhurnal 1977, 30 (2), 165-171.*
International Search Report for PCT/EP2015/057580 dated Jun. 3, 2015.
International Search Report for PCT/EP2015/057582 dated May 27, 2015.
International Search Report for PCT/EP2015/057584 dated Jun. 15, 2015.
Julia, M., et al., "Synthése de l'oxyde rose et de composés voisins", Bulletin de la SocietèChimique de France 1963, p. 1983.
Lui, C., et al., "A Novel Synthesis of cis-Dihydro-rose Oxide and Related Stereochemistry", Journal of Heterocyclic Chemistry, vol. 21, No. 1, (1984), pp. 129-132.
Romanov, N., et al., "Dehydration of 2- and 2,2-subsituted 4,4-dimethyl- and 4-methyl-4-phenyl-1,3-dioxanes", Journal of Applied Chemistry of the USSR, vol. 55, No. 1, (1982), pp. 140-143. (English translation from Zhurnal Prikladnoi Khimii, Ed. 55, No. 1, (1981), pp. 157-161).
Romanov, N., et al., "Isomerization of 2-R-4,4-dimethyl- and 2-R-4-methyl-4-phenyl-1,3-dioxanes to 2-R-4-methyl- and 2-R-4-phentltetrahydropyran-4-ols", Journal of Applied Chemistry of the USSR, vol. 56, No. 1, (1983), pp. 2526-2528. (English translation from Zhurnal Prikladnoi Khimii, Ed. 55, No. 12, (1982), pp. 2778-2780).
Schindler, G., et al., "Dihydroroseoxide—A Unique New Aroma Chemical", Perfumer & Flavorist, vol. 11, (1986), pp. 29-30.
U.S. Appl. No. 15/303,976, filed Oct. 13, 2016, Stork et al.
U.S. Appl. No. 15/304,299, filed Oct. 14, 2016, Stork et al.
International Preliminary Report on Patentability for Application No. PCT/EP2015/057580, English Translation, dated Sep. 5, 2016.
International Preliminary Report on Patentability for Application No. PCT/EP2015/057582, English Translation, dated Oct. 18, 2016.

(Continued)

*Primary Examiner* — Daniel R Carcanague
(74) *Attorney, Agent, or Firm* — Drinker Biddle & Reath LLP

(57) ABSTRACT

The invention relates to a method for producing 2-substituted 4-methyl-tetrahydropyrans of general formula (I) from starting materials containing at least one 2-substituted 4,4-dimethyl-1,3-dioxane of general formula (II).

19 Claims, No Drawings

(56) References Cited

OTHER PUBLICATIONS

International Preliminary Report on Patentability for Application No. PCT/EP2015/057584, English Translation, dated Aug. 2, 2016.
Wüst, et al., "Structure Elucidation, Enantioselective Analysis, and Biogenesis of Nerol Oxide in Pelargonium Species", *J. Agric. Food Chem.*, vol. 47, pp. 3145-3150 (1999).

* cited by examiner

PRODUCTION OF 2-SUBSTITUTED 4-METHYL-TETRAHYDROPYRANS FROM STARTING MATERIALS CONTAINING 2-ALKYL-4,4-DIMETHYL-1,3-DIOXANES

CROSS-REFERENCE TO RELATED APPLICATIONS

This application is a national stage application (under 35 U.S.C. § 371) of PCT/EP2015/057580, filed Apr. 8, 2015, which claims benefit of European Application No. 14164580.4, filed Apr. 14, 2014, both of which are incorporated herein by reference in their entirety.

BACKGROUND OF THE INVENTION

The present invention relates to a method for preparing 2-substituted 4-methyltetrahydropyrans from starting materials comprising at least one 2-alkyl-4,4-dimethyl-1,3-dioxane.

STATE OF THE ART

Alkyl-substituted tetrahydropyrans have found widespread application as aromas and flavorings. One known representative from this class is 2-(2-methyl-1-propenyl)-4-methyltetrahydropyran (rose oxide), which has a refreshing, flowery and fresh fragrance note. This fragrance varies depending on the isomers used, with each isomer possessing a characteristic note.

WO 2009/077550 describes a method for preparing cis-2-(2-methylprop-1-enyl)-4-methyltetrahydropyran comprising the catalytic hydrogenation of 2-(2-methylprop-1-enyl)-4-methylenetetrahydropyran in the presence of hydrogen and a heterogeneous catalyst comprising ruthenium on a support and subsequently bringing the compounds thus obtained into contact with a strongly acidic cation exchanger.

M. Wüst et al. describe in J. Agric. Food Chem. 1999, 47, 3145-3150, inter alia, the enantioselective synthesis of cis- and trans-rose oxide. For this purpose, the (S)-3,6-dihydro-4-methyl-2-(2-methyl-1-propenyl)-2H-pyran obtained by a Wittig reaction is subjected to a partial reduction on a microscale.

On account of its limited stability, the restrictive availability of natural rose oxide, and the laborious and hence expensive synthesis, more favorable alternatives with comparable olfactory properties have been sought. One such alternative is 2-(2-methylpropyl)-4-methyltetrahydro-2H-pyran, which is also termed dihydrorose oxide.

The first synthesis of dihydrorose oxide was described by M. Julia and B. Jacquet in Bulletin de la Societe Chimique de France 1963, 8-9, 1983. Starting from but-2-ene-1-al, a Diels-Alder reaction with ethyl vinyl ether and subsequent hydrogenation gave a cyclic acetal. Following elimination of ethanol, hydrobromination of the resulting double bond, and concluding Grignard reaction using isopropylmagnesium bromide, a racemic mixture of cis- and trans-dihydrorose oxide was obtained.

Liu et al. describe in J. Heterocyclic Chem, 21, 129-132 (1984) the preparation of cis-dihydrorose oxide by hydrogenation of 2-isobutyl-4-methyl-5,6-dihydro-4H-pyran with $PtO_2$ in acetic acid.

Schindler and Vogel describe schematically in Perfume & Flavorist, Vol 11, 29-30 (1986) the preparation of dihydrorose oxide from 3-methylbut-3-en-1-ol and 3-methylbutanal as starting material, in which a cis/trans mixture is obtained in a ratio of 70:30. Neither the reaction pathway nor the conditions to be observed are described in any more detail.

EP 0 770 670 B1 describes a perfume composition comprising 2-substituted (4R)-cis-4-methyltetrahydro-2H-pyrans. In the application, the odor properties of the isomers of rose oxide and dihydrorose oxide are described. The isomers of dihydrorose oxide are synthesized by hydrogenation of the corresponding isomers of rose oxide.

There continues to be a great need for effective methods for preparing 2-substituted 4-methyltetrahydropyrans from readily available starting materials. In addition to the synthesis of pure substances, the use of by-products from other synthetic methods, which to date cannot be used, is also of particular interest here. This includes, in particular, the integrated preparation of at least two aromas or flavorings, starting from a basic reaction.

2-substituted 4-hydroxy-4-methyltetrahydropyrans are likewise valuable compounds for use as aroma chemicals. Thus, the cis/trans diastereomeric mixture of 2-(2-methylpropyl)-4-hydroxy-4-methyltetrahydropyran, for example, is characterized

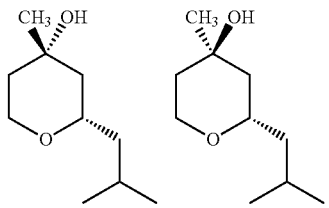

by a pleasant scent of lily of the valley and is suitable to a particular degree for use as an aroma chemical, e.g. for preparing fragrance compositions.

EP 1 493 737 A1 discloses a method for preparing mixtures of ethylenically unsaturated 4-methyl- or 4-methylenepyrans and the corresponding 4-hydroxypyrans by reacting the corresponding aldehydes with isoprenol, wherein the reaction is initiated in a reaction system in which the molar ratio of aldehyde to isoprenol is greater than 1, i.e. the aldehyde is used in excess. In addition, the document discloses the subsequent dehydration of the mixtures mentioned to the desired ethylenically unsaturated pyrans.

WO 2011/147919 describes a method for preparing 2-substituted 4-hydroxy-4-methyltetrahydropyranols and specifically 2-isobutyl-4-hydroxy-4-methyltetrahydropyran by reacting isoprenol with prenal and subsequent hydrogenation.

WO 2010/133473 describes a method for preparing 2-substituted 4-hydroxy-4-methyltetrahydropyrans of the formula (I)

(A)

where the residue $R^1$ is a straight-chain or branched alkyl or alkenyl residue having 1 to 12 carbon atoms, an optionally alkyl-substituted cycloalkyl residue having a total of 3 to 12 carbon atoms or an optionally alkyl- and/or alkoxy-substituted aryl residue having a total of 6 to 12 carbon atoms, in which isoprenol (3-methylbut-3-en-1-ol) is reacted with an aldehyde of the formula $R^1$—CHO, the reaction being conducted in the presence of water and in the presence of a strongly acidic cation exchanger.

WO 2011/154330 describes a method comparable to WO 2010/133473, in which the reaction mixture obtained is subjected to a distillative work-up in a dividing wall column or in two thermally coupled distillation columns.

As described in WO 2010/133473 and WO 2011/154330, a complex reaction mixture is obtained from the acid-catalyzed reaction of isoprenol (3-methylbut-3-en-1-ol) with an aldehyde of the formula $R^1$—CHO, which comprises, in addition to 2-substituted 4-hydroxy-4-methyltetrahydropyrans, also dehydrated by-products of the formulae (D), (E) and/or (F)

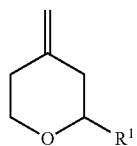
(D)

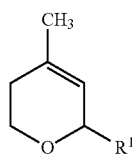
(E)

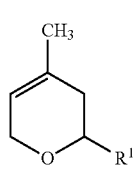
(F)

and also, as further by-products, inter alia, the 1,3-dioxanes (G).

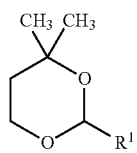
(G)

These by-products could not be used until recently for providing further materials of value, but were either discharged or were fed back again into the reaction of isoprenol with the aldehyde, together with the starting compounds used in excess. The latter is problematic owing to a potential accumulation of these components in the reaction mixture.

The international patent application PCT/EP2013/071409 (WO 2014/060345), unpublished at the priority date of the present invention, describes a method for preparing 2-substituted 4-hydroxy-4-methyltetrahydropyrans of the general formula (I) and 2-substituted 4-methyl-tetrahydropyrans of the general formula (II)

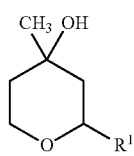
(A)

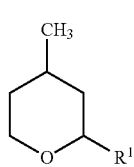
(B)

in which $R^1$ is a straight-chain or branched $C_1$-$C_{12}$-alkyl, straight-chain or branched $C_2$-$C_{12}$-alkenyl, unsubstituted or $C_1$-$C_{12}$-alkyl- and/or $C_1$-$C_{12}$-alkoxy-substituted cycloalkyl having a total of 3 to 20 carbon atoms or unsubstituted or $C_1$-$C_{12}$-alkyl- and/or $C_1$-$C_{12}$-alkoxy-substituted aryl having a total of 6 to 20 carbon atoms, in which a) 3-methylbut-3-en-1-ol is reacted in the presence of an acidic catalyst with an aldehyde of the formula $R^1$—CHO, where $R^1$ in the formula is as defined above, wherein a reaction mixture is obtained comprising at least one 2-substituted 4-hydroxy-4-methyltetrahydropyran of the general formula (A), at least one of the compounds (D), (E) or (F) and at least one dioxane compound (G)

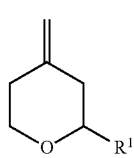
(D)

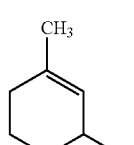
(E)

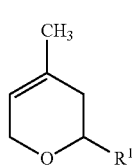
(F)

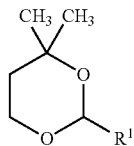
(G)

where $R^1$ is as defined above, b) the reaction product from step a) is subjected to a separation to obtain a fraction enriched in 2-substituted 4-hydroxy-4-methyltetrahydropyrans of the general formula (A) and a fraction comprising at least one of the compounds (D), (E) or (F) and at least one dioxane compound (G), c) the fraction comprising at least one of the compounds (D), (E) or (F) and at least one dioxane compound (G) is subjected to a hydrogenation, d) a fraction enriched in 2-substituted 4-methyltetrahydropyrans (B) and a fraction enriched in the at least one dioxane compound (G) are isolated from the hydrogenation product obtained in step c).

Romanov et al. describe in the Journal of Applied Chem. of the USSR, 55 (1), pp. 140-143 (1982) (English translation of Zhurnal Prikladnoi Khimii, Bd. 55, Nr. 1, 157-161 (1981)) the acid-catalyzed reaction of the dioxane compound G') to give the dihydropyrans E') and F').

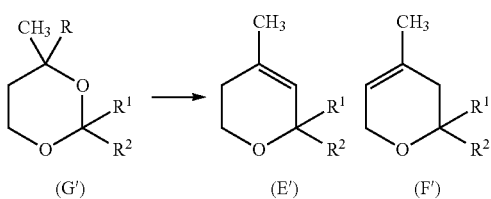

4-Methyl-2-isobutyl-5,6-dihydropyran and 4-methyl-2-isobutyl-3,6-dihydropyran are mentioned in the tables. The acidic catalysts used are $H_2SO_4$ or sulfonic acid group-containing styrene-divinylbenzene ion exchangers. The reaction is effected with dioxane compounds G') in pure form and in the presence of cyclohexane or toluene as solvent.

Romanov et al. describe in the Journal of Applied Chem. of the USSR, 56 (1), pp. 2526-2528 (1983) (English translation of Zhurnal Prikladnoi Khimii, Bd. 55, Nr. 12, 2778-2780 (1982)) the acid-catalyzed isomerization of 2-R-4,4-dimethyl- and 2-R-4-methyl-4-phenyl-1,3-dioxanes to 2-R-4,4-methyl- and 2-R-4-phenyl-1,3-tetrahydropyran-4-ols.

It is an object of the present invention to provide an improved method for preparing 2-substituted 4-methyltetrahydropyrans.

It has now been found, surprisingly, that product mixtures enriched with at least one of three isomeric dihydropyrans, characterized hereinbelow by the formulae (III.1), (III.2) and (III.3), are obtained by reacting 2-alkyl-4,4-dimethyl-1,3-dioxane-containing starting materials in the presence of a strong acid and/or an acidic ion exchanger. These product mixtures can be converted by hydrogenation into 2-substituted 4-methyltetrahydropyrans and specifically into dihydrorose oxide.

It has also been found, surprisingly, that through acidic reaction of a starting mixture which as well as the 2-alkyl-4,4-dimethyl-1,3-dioxane already includes at least one such dihydropyran of the formulae (III.1), (III.2) and (III.3), it is possible to increase further the amount of these dihydropyrans in the product mixture.

It has also been found, surprisingly, that the content of the product mixture of both the dihydropyrans of the formulae (III.1), (III.2) and/or (III.3) and the 2-substituted 4-hydroxy-4-methyltetrahydropyran (VI) may be further increased by acidic reaction of a starting mixture comprising, in addition to the 2-alkyl-4,4-dimethyl-1,3-dioxane, at least one dihydropyran (III.1), (III.2) or (III.3) and additionally at least one 2-substituted 4-hydroxy-4-methyltetrahydropyran (characterized hereinafter by the formula VI). The acid treatment according to the invention is therefore suitable for a method for the integrated preparation of 2-substituted 4-hydroxy-4-methyltetrahydropyrans and 2-substituted 4-methyltetrahydropyrans.

It was found, specifically, that the dioxane-containing sidestream (=waste stream), obtained in the acid-catalyzed preparation of 2-substituted 4-hydroxy-4-methyltetrahydropyrans by reacting isoprenol (3-methylbut-3-en-1-ol) with a suitable aldehyde (especially isovaleraldehyde), can be supplied to a large extent for use as an aroma chemical and in particular as a fragrance by way of the acid treatment according to the invention.

SUMMARY OF THE INVENTION

The invention relates to a method for preparing 2-substituted 4-methyltetrahydropyrans of the general formula (I)

in which
$R^1$ is a straight-chain or branched $C_1$-$C_{12}$-alkyl, straight-chain or branched $C_2$-$C_{12}$-alkenyl, unsubstituted or $C_1$-$C_{12}$-alkyl- and/or $C_1$-$C_{12}$-alkoxy-substituted cycloalkyl having a total of 3 to 20 carbon atoms or unsubstituted or $C_1$-$C_{12}$-alkyl- and/or $C_1$-$C_{12}$-alkoxy-substituted aryl having a total of 6 to 20 carbon atoms, in which
a) a starting material is provided comprising at least one dioxane compound of the general formula (II)

where $R^1$ is as defined above, b) the starting material is subjected to a reaction in the presence of a strong acid and/or an acidic ion exchanger, wherein, compared to the starting material, a product mixture depleted in the dioxane compound of the formula (II) and enriched in at least one of the compounds of the formulae (III.1), (III.2) or (III.3)

-continued

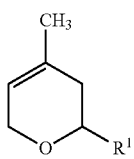
(III.3)

is obtained, where $R^1$ is as defined above,
c) the product mixture obtained in step b) is subjected to a hydrogenation.

DESCRIPTION OF THE INVENTION

The method according to the invention has the following advantages:
  using the method according to the invention, 2-alkyl-4,4-dimethyl-1,3-dioxane-containing starting materials can be used to prepare 2-substituted 4-methyltetrahydropyrans, i.e. can supply the use as an aroma chemical and particularly as a fragrance.
  the product mixtures obtained by the acid treatment according to the invention are characterized by their low residual content of 2-alkyl-4,4-dimethyl-1,3-dioxanes. The problems known from the prior art in the separation and/or further processing of such dioxane-containing streams are avoided or considerably reduced.
  using the method according to the invention, a large part of the present sidestream (waste stream) in the acid-catalyzed preparation of 2-substituted 4-hydroxy-4-methyltetrahydropyrans can specifically be used as material of value. On account of the problems described above in the separation of dihydropyrans of the formulae (III.1), (III.2) and/or (III.3) present in this sidestream on the one hand and of 2-alkyl-4,4-dimethyl-1,3-dioxanes (II) on the other hand, this sidestream has, until now, generally been fed to a combustion process.
  the hydrogenation envisaged according to the invention opens access to 2-substituted 4-methyltetrahydropyrans, and especially to dihydrorose oxide, and requires only two reaction stages, starting from the sidestream.
  for the preparation of the 2-substituted 4-methyltetrahydropyrans, especially of dihydrorose oxide, there is no need to use further expensive and/or potentially hazardous reagents, such as, for instance, Grignard reagents or complex hydrides, such as lithium aluminum hydride.

Unless otherwise specified in more detail below, the terms
"2-substituted 4-methyltetrahydropyran",
"2-(2-methylpropyl)-4-methyltetrahydropyran" (="dihydrorose oxide"),
"2-substituted 4-hydroxy-4-methyltetrahydropyran",
"2-(2-methylpropyl)-4-hydroxy-4-methyltetrahydropyran",
in the context of the invention, refer to cis/trans mixtures of any composition and also the pure conformational isomers. The terms mentioned above also refer to all enantiomers in pure form and also racemic and optically active mixtures of the enantiomers of these compounds.

If, in the following, cis and trans diastereoisomers of the compounds (I) or (II) are in question, only one of the enantiomeric forms is shown in each case. For the purposes of illustration only, the isomers of 2-(2-methylpropyl)-4-methyltetrahydropyran (I) (dihydrorose oxide) are shown below:

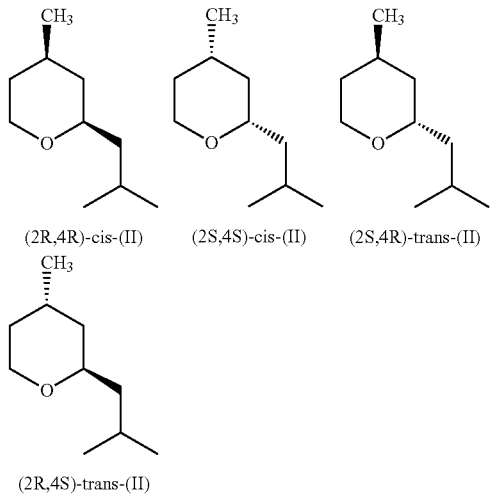

(2R,4R)-cis-(II)     (2S,4S)-cis-(II)     (2S,4R)-trans-(II)

(2R,4S)-trans-(II)

In the context of the present invention, the expression straight-chain or branched alkyl preferably represents $C_1$-$C_6$-alkyl and particularly preferably $C_1$-$C_4$-alkyl. In particular, alkyl is methyl, ethyl, n-propyl, isopropyl, n-butyl, isobutyl (2-methylpropyl), sec-butyl (1-methylpropyl), tert-butyl (1,1-dimethylethyl), n-pentyl or n-hexyl. Alkyl is especially methyl, ethyl, n-propyl, isopropyl, or isobutyl.

In the context of the present invention, the expression straight-chain or branched alkoxy preferably represents $C_1$-$C_6$-alkoxy and particularly preferably $C_1$-$C_4$-alkoxy. In particular, alkoxy is methoxy, ethoxy, n-propyloxy, isopropyloxy, n-butyloxy, isobutyloxy, sec-butyloxy, tert-butyloxy, n-pentyloxy or n-hexyloxy. Alkoxy is especially methoxy, ethoxy, n-propyloxy, isopropyloxy, or isobutyloxy.

In the context of the present invention, the expression straight-chain or branched alkenyl preferably represents $C_2$-$C_6$-alkenyl and particularly preferably $C_2$-$C_4$-alkenyl. The alkenyl residue has, in addition to single bonds, one or more, preferably 1 to 3, particularly preferably 1 or 2 and especially preferably one ethylenic double bond. In particular, alkenyl is ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl.

In the context of the invention, cycloalkyl refers to a cycloaliphatic residue preferably having 3 to 10, particularly preferably 5 to 8 carbon atoms. Examples of cycloalkyl groups are, particularly, cyclopropyl, cyclobutyl, cyclopentyl, cyclohexyl, cycloheptyl or cyclooctyl. Cycloalkyl is especially cyclohexyl.

Substituted cycloalkyl groups may have one or more substituents (e.g. 1, 2, 3, 4 or 5) depending on the size of the ring. These are each preferably independently selected from $C_1$-$C_6$-alkyl and $C_1$-$C_6$-alkoxy. In the case of substitution, the cycloalkyl groups preferably bear one or more, for example one, two, three, four or five $C_1$-$C_6$-alkyl groups. Examples of substituted cycloalkyl groups are particularly 2- and 3-methylcyclopentyl, 2- and 3-ethylcyclopentyl, 2-, 3- and 4-methylcyclohexyl, 2-, 3- and 4-ethylcyclohexyl, 2-, 3- and 4-propylcyclohexyl, 2-, 3- and 4-isopropylcyclohexyl, 2-, 3- and 4-butylcyclohexyl and 2-, 3- and 4-isobutylcyclohexyl.

In the context of the present invention, the expression "aryl" comprises mono- or polycyclic aromatic hydrocarbon residues typically having 6 to 18, preferably 6 to 14, particularly preferably 6 to 10 carbon atoms. Examples of aryl are particularly phenyl, naphthyl, indenyl, fluorenyl, anthracenyl, phenanthrenyl, naphthacenyl, chrysenyl, pyrenyl, etc., and especially phenyl or naphthyl.

Substituted aryls may have one or more substituents (e.g. 1, 2, 3, 4 or 5) depending on the number and size of their ring systems. These are each preferably independently selected from $C_1$-$C_6$-alkyl and $C_1$-$C_6$-alkoxy. Examples of substituted aryl residues are 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-disec-butylphenyl, 2,4,6-trisec-butylphenyl, 2-, 3- and 4-tert-butylphenyl, 2,4-, 2,5-, 3,5- and 2,6-di-tert-butylphenyl and 2,4,6-tri-tert-butylphenyl.

In the compounds of the formulae (I), (II), (III.1), (III.2), (III.3), (V), and (VI), $R^1$ is preferably a straight-chain or branched $C_1$-$C_{12}$-alkyl or straight-chain or branched $C_2$-$C_{12}$-alkenyl. Particularly preferably, $R^1$ is a straight-chain or branched $C_1$-$C_6$-alkyl or straight-chain or branched $C_2$-$C_6$-alkenyl. In a further preferred embodiment, $R^1$ is phenyl.

Preferred definitions in accordance with the invention for the residue $R^1$ therefore are, for example, methyl, ethyl, n-propyl, isopropyl, n-butyl, isobutyl, n-pentyl, n-hexyl or n-heptyl, preferably methyl, ethyl, n-propyl, isopropyl, n-butyl, isobutyl, especially preferably isobutyl (2-methylpropyl).

In the context of a preferred embodiment, the present invention therefore relates to a method for preparing and isolating 2-(2-methylpropyl)-4-methyltetrahydropyran of the formula (Ia) (dihydrorose oxide).

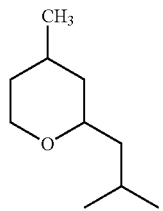

(I.a)

Step a)

Suitable starting materials for use in step a) may comprise at least one dioxane compound of the general formula (II)

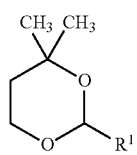

(II)

where $R^1$ is as defined above, in essentially pure form. Essentially pure form is understood to mean that the starting material used in step a) preferably comprises at least 90% by weight, particularly preferably at least 95% by weight, particularly at least 99% by weight of at least one dioxane compound of the general formula (II), based on the total weight of the starting material.

Suitable methods for preparing 1,3-dioxanes of the formula (II) are in principle known to those skilled in the art. This includes, for example, the reaction of 3-methyl-1,3-butanediol with suitably substituted aldehydes according to the following scheme:

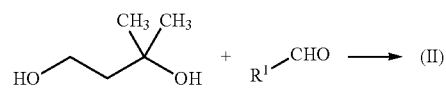

3-Methyl-1,3-butanediol is commercially available, e.g. from Sigma Aldrich. The same applies to many aldehydes of the formula $R^1$—CHO.

A starting material is preferably provided in step a) which comprises at least a further component in addition to at least one dioxane compound (II).

The starting material provided in step a) is preferably a natural or synthetic product mixture from the synthesis and/or the isolation of an aroma or flavouring other than 2-substituted 4-methyl-tetrahydropyrans of the general formula (I).

The starting material provided in step a) preferably comprises the at least one dioxane compound (II) in an amount of 1 to 99% by weight, preferably 2 to 90% by weight, particularly 5 to 50% by weight, especially 15 to 50% by weight, based on the total weight of the starting material.

In a preferred embodiment, a starting material is provided in step a) which comprises at least one of the compounds of the formulae (III.1), (III.2) or (III.3) in addition to at least one dioxane compound (II),

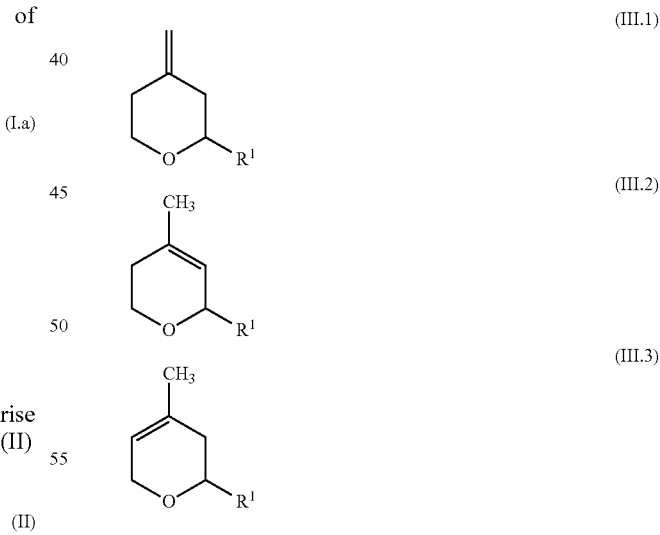

in which
$R^1$ is a straight-chain or branched $C_1$-$C_{12}$-alkyl, straight-chain or branched $C_2$-$C_{12}$-alkenyl, unsubstituted or $C_1$-$C_{12}$-alkyl- and/or $C_1$-$C_{12}$-alkoxy-substituted cycloalkyl having a total of 3 to 20 carbon atoms or unsubstituted or $C_1$-$C_{12}$-alkyl- and/or $C_1$-$C_{12}$-alkoxy-substituted aryl having a total of 6 to 20 carbon atoms.

Product mixtures comprising at least one of the dihydropyran compounds of the formulae (III.1), (III.2) or (III.3), may be converted by hydrogenation, as stated above, to 2-substituted 4-methyltetrahydropyrans and especially to dihydrorose oxide. The content of the product mixture obtained of compounds of the formulae (III.1), (III.2) and (III.3) can be further advantageously increased, compared to the starting material, by reaction of a starting material comprising at least one dioxane compound (II) and at least one of the compounds of the formulae (III.1), (III.2) or (III.3) in the presence of a strong acid and/or an acidic ion exchanger. At the same time a product mixture is obtained which is depleted in the dioxane compound of the formula (II), relative to the starting material.

The starting material provided in step a) preferably comprises the compounds of the formulae (III.1), (III.2) and/or (III.3) in a total amount of 1 to 99% by weight, preferably 5 to 95% by weight, particularly 15 to 70% by weight, based on the total weight of the starting material.

In a typical composition, the starting material provided in step a) comprises the following compounds, based in each case on the total weight of the reaction mixture:
Isovaleraldehyde: 0-15% by weight,
Isoprenol: 0-15% by weight,
Dioxane compound (II): 15-50% by weight,
Compounds of the formulae (III.1), (III.2) and/or (III.3): in total 15-70% by weight,
Acetals other than (II): 0-5% by weight,
2-substituted 4-hydroxy-4-methyltetrahydropyrans (VI): 0-30% by weight,
Water: 0-10% by weight.

A specific embodiment is a method in which, to provide the starting material in step a):
a1) 3-Methylbut-3-en-1-ol of the formula (IV)

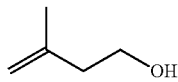

(IV)

is reacted in the presence of an acidic catalyst with an aldehyde of the formula (V)

(V)

in which
R¹ is a straight-chain or branched $C_1$-$C_{12}$-alkyl, straight-chain or branched $C_2$-$C_{12}$-alkenyl, unsubstituted or $C_1$-$C_{12}$-alkyl- and/or $C_1$-$C_{12}$-alkoxy-substituted cycloalkyl having a total of 3 to 20 carbon atoms or unsubstituted or $C_1$-$C_{12}$-alkyl- and/or $C_1$-$C_{12}$-alkoxy-substituted aryl having a total of 6 to 20 carbon atoms, wherein a reaction mixture is obtained comprising at least one dioxane compound (II), at least one of the compounds (III.1), (III.2) or (III.3), and at least one 2-substituted 4-hydroxy-4-methyltetrahydropyran of the general formula (VI)

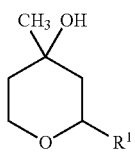

(VI)

where R¹ in the formula (VI) is as defined above, a2) optionally the reaction mixture from step a1) is subjected to a separation to obtain at least one fraction enriched in 2-substituted 4-hydroxy-4-methyltetrahydropyrans of the general formula (VI) and a fraction comprising the dioxane compound (II) and at least one of the compounds (III.1), (III.2) or (III.3), and the reaction product obtained in step a1), or the fraction which is obtained in step a2) and which comprises the dioxane compound (II) and at least one of the compounds (III.1), (III.2) or (III.3), is used as starting material for preparing the 2-substituted 4-methyltetrahydropyrans of the formula (I).

Special preference is given to a method, wherein, in order to provide the starting material in step a):
a1) 3-Methylbut-3-en-1-ol of the formula (IV)

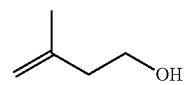

(IV)

is reacted in the presence of an acidic catalyst with an aldehyde of the formula (V)

(V)

in which
R¹ is a straight-chain or branched $C_1$-$C_{12}$-alkyl, straight-chain or branched $C_2$-$C_{12}$-alkenyl, unsubstituted or $C_1$-$C_{12}$-alkyl- and/or $C_1$-$C_{12}$-alkoxy-substituted cycloalkyl having a total of 3 to 20 carbon atoms or unsubstituted or $C_1$-$C_{12}$-alkyl- and/or $C_1$-$C_{12}$-alkoxy-substituted aryl having a total of 6 to 20 carbon atoms, wherein a reaction mixture is obtained comprising at least one dioxane compound (II), at least one of the compounds (III.1), (III.2) or (III.3), and at least one 2-substituted 4-hydroxy-4-methyltetrahydropyran of the general formula (VI)

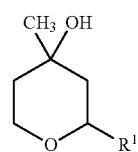

(VI)

where R¹ in the formula (VI) is as defined above,
a2) the reaction mixture from step a1) is subjected to a separation to obtain at least one fraction enriched in 2-substituted 4-hydroxy-4-methyltetrahydropyrans of the general formula (VI) and a fraction comprising the dioxane compound (II) and at least one of the compounds (III.1), (III.2) or (III.3),
and the fraction obtained in step a2), comprising the dioxane compound (II) and at least one of the compounds (III.1), (III.2) or (III.3), is used as starting material to prepare the 2-substituted 4-methyltetrahydropyrans of the formula (I).

Advantageously, the above-stated especially preferred embodiment permits an integrated method for the simultaneous preparation of 2-substituted 4-methyltetrahydropyrans and of 2-substituted 4-hydroxy-4-methyltetrahydropyrans.

In one especially preferred embodiment, therefore, the present invention relates to a method for preparing and isolating 2-(2-methylpropyl)-4-methyltetrahydropyran of the formula (Ia) (dihydrorose oxide) and 2-(2-methylpropyl)-4-hydroxy-4-methyltetrahydropyran of the formula (IIa):

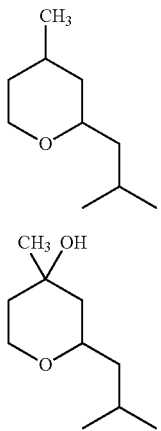

Step a1)

One of the starting materials for step a1) of the method according to the invention is 3-methylbut-3-en-1-ol (isoprenol) of the formula (IV),

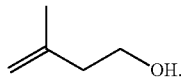

Isoprenol is readily accessible on any scale from isobutene and formaldehyde by known methods and is commercially available. There are no particular requirements regarding the purity, quality or preparation process of the isoprenol to be used according to the invention. It may be used at commercial quality and purity in step a) of the method according to the invention. Isoprenol is preferably used having a purity of 90% by weight or more, particularly preferably having a purity of 95 to 100% by weight and especially preferably having a purity of 97 to 99.9% by weight or still more preferably 98 to 99.8% by weight.

A further starting material for step a1) of the method according to the invention is an aldehyde of the formula (V) $R^1$—CHO, where $R^1$ in the formula (V) is as defined above.

Preferred aldehydes of the formula (V) to be used are: acetaldehyde, valeraldehyde, isovaleraldehyde, pentanol, hexanol, heptanal, benzaldehyde, citral, citronellal. Especially preferred aldehydes of the formula (V) to be used according to the invention are isovaleraldehyde and benzaldehyde, particularly isovaleraldehyde.

The 3-methylbut-3-enol (IV) and the aldehyde (V) in step a1) are preferably used in a molar ratio of about 1 to 2 to 2 to 1, particularly preferably 0.7 to 1 to 2 to 1, particularly 1 to 1 to 2 to 1. In a specific embodiment, the 3-methylbut-3-enol (IV) and the aldehyde (V) in step a) are used in a molar ratio of 1 to 1 to 1.5 to 1.

The reaction in step a1) preferably takes place in the presence of an acidic catalyst. In principle, any acidic catalyst can be used for the reaction in step a1), i.e. any substance having Brönstedt or Lewis acidity. Examples of suitable catalysts are protic acids such as hydrochloric acid, sulfuric acid, phosphoric acid, methanesulfonic acid and p-toluenesulfonic acid, acidic molecular elemental compounds such as aluminum chloride, boron trifluoride, zinc chloride, phosphorus pentafluoride, arsenic trifluoride, tin tetrachloride, titanium tetrachloride and antimony pentafluoride; oxidic acidic solids such as zeolites, silicates, aluminates, aluminosilicates, clays and acidic ion exchangers.

The acidic catalyst used in step a1) is preferably selected from hydrochloric acid, sulfuric acid, methanesulfonic acid, p-toluenesulfonic acid and strongly acidic cation exchangers.

In a first version, the reaction in step a1) takes place in the presence of a Brönstedt acid preferably selected from hydrochloric acid, sulfuric acid, methanesulfonic acid, p-toluenesulfonic acid. In this first version, a solvent may be used in step a1) preferably selected from hydrocarbons and hydrocarbon mixtures. Suitable solvents are, for example, hexane, heptane, naphtha, petroleum ether, cyclohexane, decalin, toluene, xylene and mixtures thereof. Solvent is preferably not used. In this first version, the catalyst is preferably used in an amount of 0.05 to 5 mol %, particularly preferably 0.1 to 4 mol %, based on the aldehyde (V). The reaction is preferably effected in step a1) according to this first version at a temperature in the range of 20 to 120° C., particularly preferably 30 to 80° C.

In a second version, the reaction in step a1) is effected in the presence of a strongly acidic cation exchanger. The term strongly acidic cation exchanger is understood to mean a cation exchanger in the $H^+$ form having strongly acidic groups. Strongly acidic groups are generally sulfonic acid groups. The acidic groups are generally attached to a polymer matrix which may be, for example, in gel form or macroporous. A preferred embodiment of the method according to the invention is accordingly characterized in that a strongly acidic cation exchanger having sulfonic acid groups is used. Suitable strongly acidic cation exchangers are described in WO 2010/133473 and WO 2011/154330, which are hereby fully incorporated by reference.

Suitable for use in step a1) are strongly acidic ion exchangers (e.g. Amberlyst, Amberlite, Dowex, Lewatit, Purolite, Serdolit), which are based on polystyrene and the copolymers of styrene and divinylbenzene as support matrix, comprising sulfonic acid groups in $H^+$ form and ion exchange groups functionalized with sulfonic acid groups (—$SO_3H$). The ion exchangers differ in the structure of their polymer skeleton and a distinction is made between gel-like and macoporous resins. In a specific embodiment, a perfluorinated polymeric ion exchange resin is used in step a). Such resins are marketed, for example under the name Nafion® by DuPont. An example of such a perfluorinated polymeric ion exchange resin which may be mentioned is Nafion® NR-50.

Suitable commercially available strongly acidic cation exchangers for the reaction in step a1) are known, for example, under the trade names Lewatit® (Lanxess), Purolite® (The Purolite Company), Dowex® (Dow Chemical Company), Amberlite® (Rohm and Haas Company), Amberlyst™ (Rohm and Haas Company). Preferred strongly acidic cation exchangers are: Lewatit® K 1221, Lewatit® K 1461, Lewatit® K 2431, Lewatit® K 2620, Lewatit® K 2621, Lewatit® K 2629, Lewatit® K 2649, Amberlite® FPC 22, Amberlite® FPC 23, Amberlite® IR 120, Amberlyst™ 131, Amberlyst™ 15, Amberlyst™ 31, Amberlyst™ 35, Amberlyst™ 36, Amberlyst™ 39, Amberlyst™ 46, Amberlyst™ 70, Purolite® SGC650, Purolite® C100H, Purolite® C150H, Dowex® 50X8, Serdolit® red and Nation® NR-50.

The strongly acidic ion exchange resins are generally regenerated using hydrochloric acid and/or sulfuric acid.

In a specific embodiment, the 3-methylbut-3-enol (IV) and the aldehyde (V) are reacted in step a1) in the presence of a strongly acidic cation exchanger and in the presence of water. According to a specific embodiment, water is also additionally added to the reaction mixture besides isoprenol (IV) and the aldehyde of the formula (V).

In a suitable configuration, the starting materials are reacted in the presence of at least 25 mol %, preferably at least 50 mol % water. The starting materials are reacted, for example, in the presence of 25 to 150 mol %, preferably 40 to 150 mol %, particularly preferably 50 to 140 mol %, particularly 50 to 80 mol % water. In this case, the amount of water used refers to the amount of substance of the starting material optionally used in less quantity or, in the case of an equimolar reaction, in equal amount of either.

The reaction is preferably carried out in the presence of at least about 3% by weight, particularly preferably at least 5% by weight of added water. The alcohol of the formula (IV) and the aldehyde of the formula (V) are reacted, for example, in the presence of 3% to 15% by weight of water, preferably 5% to 12% by weight of water. The % by weight specified above are based in this case on the total amount of the reaction mixture, comprising the compounds of the formulae (IV) and (V) and also water.

The amount of water can be freely selected above the stated values, and is only limited, if at all, by process technology or economic aspects and may be used in quite large excess, for example, 5 to 15-fold or above. A mixture of isoprenol (IV) and the aldehyde of the formula (V), preferably isovaleraldehyde, is preferably prepared with the amount of water to be added such that the water added to the mixture of isoprenol and the aldehyde remains dissolved, i.e. a biphasic system is not present.

To react isoprenol (IV) with the aldehyde (V) in step a1), the starting materials mentioned and optionally the added water may be brought into contact with the acidic cation exchanger. Isoprenol (IV), aldehyde (V) and optionally the added water are preferably used in the form of a mixture in step a). The starting materials mentioned, i.e. isoprenol (IV) and the aldehyde (V) and the water to be used in the aforementioned amount may be brought into contact or mixed in any sequence.

The amount of strongly acidic cation exchanger in step a1) is not critical and may be freely selected over a wide range taking into account the economic and process technology aspects. The reaction may accordingly be carried out either in the presence of catalytic amounts or in the presence of large excesses of the strongly acidic cation exchanger. The strongly acidic cation exchanger is typically used in an amount of about 5 to about 40% by weight, preferably in an amount of about 20 to about 40% by weight and particularly preferably in an amount of about 20 to about 30% by weight, based in each case on the sum total of isoprenol (IV) and aldehyde of the formula (V) used. The figures here refer to the ready-to-use cation exchanger which is generally pretreated with water and may accordingly comprise amounts of up to about 70% by weight, preferably about 30 to about 65% by weight and particularly preferably about 40 to about 65% by weight of water. Particularly in batchwise method procedures, addition of excess amounts of water are superfluous when carrying out the method according to the invention. The strongly acidic cation exchangers mentioned may be used both individually and in the form of mixtures in step a1).

In continuous mode, the catalyst hourly space velocity is, for example, in the range of 50 to 2500 mol per m³ of catalyst per hour, preferably in the range of 100 to 2000 mol per m³ of catalyst per hour, particularly in the range of 130 to 1700 mol per m³ of catalyst per hour, where the amount of substance in moles refers to the starting material of the formula (IV).

The reaction in the presence of a strongly acidic cation exchanger in step a1) may optionally also be carried out additionally in the presence of a solvent inert under the reaction conditions. Suitable solvents are, for example, tert-butyl methyl ether, cyclohexane, decalin, hexane, heptane, naphtha, petroleum ether, toluene or xylene. Said solvents can be used alone or in the form of mixtures with one another. The reaction in step a1) is preferably carried out in the presence of a strongly acidic cation exchanger without addition of an organic solvent.

The reaction of isoprenol (IV) with the selected aldehyde (V) in step a1) is preferably carried out in the presence of water and in the presence of a strongly acidic cation exchanger at a temperature in the range of 0 to 70° C., particularly preferably at a temperature in the range of 20 to 70° C. and particularly at a temperature in the range of 20 to 60° C. Here, the temperature refers to the reaction mixture.

The reaction is step a1) can be carried out in batchwise mode or continuously. In the batchwise case, for example, the reaction may be conducted such that a mixture of isoprenol (IV), the aldehyde (V), optionally water and optionally an organic solvent is charged in a suitable reaction vessel and the acidic catalyst is added. After completion of the reaction, the catalyst can be removed from the reaction mixture obtained by suitable separation methods. The sequence of bringing into contact of the individual components is not critical and may be varied in accordance with the respective process technology configuration. If a Brönstedt acid is used as catalyst in step a1), preferably selected from hydrochloric acid, sulfuric acid, methanesulfonic acid, p-toluenesulfonic acid, the catalyst can be removed, for example, by distillation after aqueous work-up, or directly by distillation. If a strongly acidic cation exchanger is used as catalyst in step a1), the catalyst can be removed, for example, by filtration or by centrifugation.

In the context of a preferred embodiment, the reaction of isoprenol (IV) with the aldehyde (V) in step a) is carried out continuously. For this purpose, a mixture, for example, of the starting materials isoprenol and aldehyde of the formula (IV) to be reacted may be prepared with water and this mixture can be brought into contact continuously with a strongly acidic cation exchanger. For instance, the selected cation exchanger may be introduced into a suitable flow reactor, for example, a stirred reactor with inlet and outlet or a tubular reactor and the starting materials and the water may be continuously supplied thereto and the reaction mixture may be continuously discharged. Here, the starting materials and the water may optionally be introduced into the flow reactor as individual components or also in the form of a mixture as previously described. Methods of this kind are described in the European patent applications 13165767.8 and 13165778.5.

The reaction mixture obtained according to the invention in step a1) comprises, in addition to at least one dioxane compound of the general formula (II),

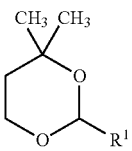

(II)

at least one of the compounds of the formulae (III.1), (III.2) or (III.3)

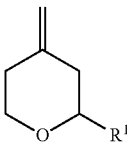

(III.1)

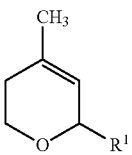

(III.2)

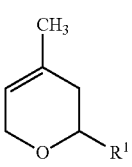

(III.3)

and at least one 2-substituted 4-hydroxy-4-methyltetrahydropyran of the general formula (VI)

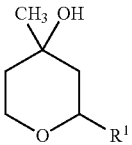

(VI)

where $R^1$ in the formulae (II), (III.1), (III.2), (III.3) and (VI) is as defined above. $R^1$ is preferably isobutyl. Generally, the reaction mixture comprises a mixture of the compounds (III.1), (III.2) and (III.3).

The reaction mixture obtained in the method according to the invention in step a1) may comprise at least one further by-product, e.g. an acetal (VII)

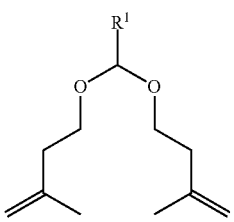

(VII)

where $R^1$ is as defined above. $R^1$ is preferably isobutyl.

The reaction mixture obtained in the method according to the invention in step a1) may comprise further components, such as unreacted 3-methylbut-3-en-1-ol (IV), unreacted aldehyde (V), water, organic solvent, etc.

The reaction mixture obtained in step a1) preferably comprises the dioxane compound of the formula (II) in a total amount of 5 to 20% by weight, particularly preferably 5 up to about 15% by weight, based on the total weight of the reaction mixture.

The reaction mixture obtained in step a1) preferably comprises the compounds of the formulae (III.1), (III.2) and (III.3) in a total amount of 5 to 20% by weight, particularly preferably 5 up to about 15% by weight, based on the total weight of the reaction mixture.

The reaction mixture obtained in step a1) preferably comprises the 2-substituted 4-hydroxy-4-methyltetrahydropyran of the formula (VI) in an amount of 50 to 90% by weight, particularly preferably 60 up to about 80% by weight, based on the total weight of the reaction mixture.

In a typical composition, the reaction mixture obtained in step a1) comprises the following compounds, based in each case on the total weight of the reaction mixture:

Isovaleraldehyde: 0-5% by weight,
Isoprenol: 0-10% by weight,
Dioxane compound (II): 5-15% by weight,
Compounds of the formulae (III.1), (III.2) and/or (III.3): in total 5-15% by weight,
Acetals other than (II): 0-5% by weight,
trans-(VI): 15-22% by weight,
cis-(VI): 45-65% by weight,
Water: 2-10% by weight, The reaction mixture obtained in step a1) preferably comprises the 2-substituted 4-hydroxy-4-methyltetrahydropyrans of the formula (VI) in the form of mixtures of the cis-diastereoisomers of the formula cis-(I) and the trans-diastereoisomers of the formula trans-(I)

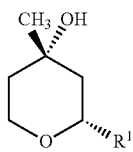

cis-(I)

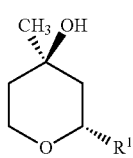

trans-(I)

where the diastereoisomeric ratio of the cis-diastereoisomers cis-(VI) to the trans-diastereoisomers trans-(VI) is preferably 65 to 35 to 95 to 5, particularly preferably 70 to 30 to 85 to 15 and $R^1$ is again defined as above.

The reaction mixture obtained in step a1) preferably comprises the 2-isobutyl-4-hydroxy-4-methyltetrahydropyran in the form of mixtures of the cis-diastereoisomers of the formula cis-(VI.a) and of the trans-diastereoisomers of the formula trans-(VI.a)

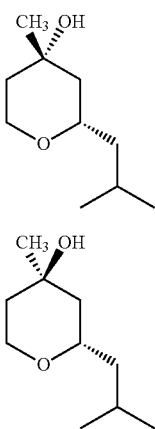

where the diastereoisomeric ratio of the cis-diastereoisomer cis-(VIa) to the trans-diastereoisomer trans-(VIa) is preferably 65 to 35 to 95 to 5, particularly preferably 70 to 30 to 85 to 15.

Such mixtures are suitable to a particular degree, on account of their particular odor properties, for use as aroma chemicals, for example, as components with scent of lily of the valley for preparing fragrance compositions.

Step a2)

The reaction mixture obtained in step a1) may be used in a first embodiment without further separation for the reaction in step b).

In a second, preferred embodiment, the reaction mixture obtained in step a1) is subjected to a separation to obtain at least one fraction enriched in 2-substituted 4-hydroxy-4-methyltetrahydropyrans of the general formula (VI) and a fraction comprising the dioxane compound (II) and at least one of the compounds (III.1), (III.2) or (III.3). The fraction comprising the dioxane compound (II) and at least one of the compounds (III.1), (III.2) or (III.3) is preferably used as starting material for the reaction in step b).

The reaction product from step a1) used for the separation in step a2) typically comprises, based on the total weight, 45 to 65% by weight of the cis-diastereoisomers cis-(VI), 15 to 22% by weight of the trans-diastereoisomers trans-(VI), 10 to 40% by weight of compounds lower boiling than the compounds (VI), 1 to 3% by weight of compounds higher boiling than the compounds (VI). The reaction product from step a1) is preferably largely free from compounds having a boiling point close to that of the stereoisomeric compounds (VI). In the context of the invention, largely free from compounds having a boiling point close to that of the stereoisomeric compounds (VI) means that the reaction product from step a1) comprises at most 1% by weight, particularly preferably at most 0.5% by weight, particularly at most 0.1% by weight of compounds having a boiling point close to that of the stereoisomeric compounds (VI).

The reaction product from step a1) used for the separation in step a2) preferably comprises 45 to 65% by weight of the cis-diastereoisomers of 2-isobutyl-4-hydroxy-4-methyltetrahydropyran of the formula cis-(VI.a), 15 to 20% by weight of the trans-diastereoisomers of the formula trans-(VI.a), 20 to 40% by weight of compounds lower boiling than the compounds (VI), 1 to 3% by weight of compounds higher boiling than the compounds (VI).

The reaction mixture from step a1) of the method according to the invention is preferably subjected to a distillative separation in step a2). Suitable apparatuses for distillative separation comprise distillation columns such as tray columns, which may be equipped with bubble-caps, sieve plates, sieve trays, structured packings, random packings, valves, side draws, etc., evaporators such as thin film evaporators, falling film evaporators, forced circulation evaporators, Sambay evaporators etc. and combinations thereof.

The distillation columns may have separating internals, preferably selected from separating trays, stacked packings, e.g. sheet metal or fabric packings such as Sulzer Mellapak®, Sulzer BX, Montz B1 or Montz A3 or Kühni Rombopak, or random beds of random packings such as Dixon rings, Raschig rings, High-Flow rings or Raschig Super rings. Proven particularly useful are stacked packings, preferably sheet metal or fabric packings having a specific surface area of 100 to 750 $m^2/m^3$, particularly 250 to 500 $m^2/m^3$. They create high separation performance at low pressure drops.

An apparatus is preferably used for the separation in step a2), which comprises
- a feed column with a rectifying section situated above the feed point and a stripping section situated below the feed point,
- an upper combining column which communicates with the upper end of the rectifying section and a lower combining column which communicates with the lower end of the stripping section, and
- a draw column which communicates with the upper combining column and the lower combining column.

The separation in step a2) is preferably carried out by
(i) introducing the reaction product from step a1) into a feed column with a rectifying section situated above the feed point and a stripping section situated below the feed point,
(ii) providing an upper combining column, which communicates with the upper end of the rectifying section, with a condenser and a lower combining column, which communicates with the lower end of the stripping section, with a heater at the lower end of the column,
iii) providing a draw column, which communicates with the upper combining column and the lower combining column, which has at least one side draw,
iv) removing compounds lighter boiling than the 2-substituted 4-hydroxy-4-methyltetrahydropyrans (VI) from the top or in the upper region of the draw column, removing at least a portion of the 2-substituted 4-hydroxy-4-methyltetrahydropyrans (VI) as at least one side draw and removing the 2-substituted 4-hydroxy-4-methyltetrahydropyrans (VI), which are not drawn off as side draw, from the bottom or the lower region of the lower combining column, and removing the compounds higher boiling than the 2-substituted 4-hydroxy-4-methyltetrahydropyrans (VI).

In a preferred embodiment, the draw-off taken from the top or in the upper region of the draw column comprises:
- at least a portion or the total amount of the dioxane compound (II) present in the reaction product from step a1),
- at least a portion or the total amount of the compounds (III.1), (III.2) and (III.3) present in the reaction product from step a1),
- if present, unreacted 3-methylbut-3-en-1-ol of the formula (IV),
- if present, unreacted aldehyde (V),
- low amounts of or no 4-hydroxy-4-methyltetrahydropyrans (VI),
- water.

In a particularly preferred embodiment, 3-methylbut-3-en-1-ol of the formula (IV) and isovaleraldehyde (V) are used for the reaction in step a1). The draw-off taken from the top or in the upper region of the draw column then comprises:
- at least a portion or the total amount of the dioxane compound (II) present in the reaction product from step a), where $R^1$ is isobutyl,
- at least a portion or the total amount of the compounds (III.1), (III.2) and (III.3) present in the reaction product from step a), where $R^1$ is isobutyl,
- if present, unreacted 3-methylbut-3-en-1-ol of the formula (IV),
- if present, unreacted isovaleraldehyde (V.a),
- low amounts of or no 2-(2-methylpropyl)-4-hydroxy-4-methyltetrahydropyran of the formula (VI.a),
- water.

The top product so obtained may be subjected to a phase separation to remove the majority of the water. Apart from such a phase separation, the top product thus obtained may generally be used for the reaction in step b) without further work-up. If desired, the top product may be subjected to a further work-up to remove at least a portion of the components different from the compounds (III.1), (III.2), (III.3). For this purpose, the top product may, for example, be subjected to a further distillative separation.

In a preferred embodiment, a sidestream is drawn off from the draw column or two sidestreams are drawn off from the draw column. In a specific embodiment, only one sidestream is drawn off from the draw column.

If more than one draw-off is taken in step a2) comprising 2-substituted 4-hydroxy-4-methyltetrahydropyrans (I), e.g., two different side draw-offs or one side draw-off and one bottom draw-off, these thus generally differ with respect to the composition of the stereoisomers. It is therefore possible to isolate, compared to the reaction product, a fraction enriched in cis-diastereoisomers and a fraction enriched in trans-diastereoisomers from step a1). With sufficient separation performance of the distillation apparatus used, at least one of the diastereoisomers may be obtained in pure form if desired.

The feed column, draw column, upper combining column and lower combining column may be discrete components or may take the form of a section or chambers of a distillation column which combines several functions. The expression "columns which communicate" means that an exchange both of rising vapors and falling condensate takes place between them.

In a preferred embodiment of the method according to the invention, the distillative separation in step a2) takes place in an arrangement of distillation columns comprising a dividing wall column or an interconnection of at least two thermally coupled conventional distillation columns.

Dividing wall columns are special distillation columns having at least one feed point and at least three offtake points in which the so-called rectification region is located between evaporator and condenser, where a portion of the liquid condensate formed in the condenser moves downward as runback in countercurrent to the vapor rising from the evaporator, and which have at least one longitudinal dividing facility (dividing wall) in a subregion of the column below and/or above the feed point to prevent transverse mixing of liquid stream and/or vapor stream and which thus make it possible to separate mixtures by distillation. The basic principle of dividing wall columns is well known and is described, for example, in U.S. Pat. No. 2,471,134, EP-A-0 122 367 or in G. Kaibel, Chem. Eng. Technol. Vol. 10, 1987, pp. 92 to 98.

The general basic structure of a dividing wall column comprises at least one lateral feed point on one side of the dividing wall and at least three offtake points, of which at least one is located on the other side of the dividing wall. Since, in this type of construction, transverse mixing of liquid stream and/or vapor stream is prevented in the region of the dividing wall, it is possible to obtain the side products in pure form. This generally reduces the total number of distillation columns required in the fractionation of multicomponent mixtures. In addition, capital costs and also energy can be saved when using dividing wall columns instead of a simple connection in series of two conventional distillation columns (see M. Knott, Process Engineering, Vol. 2, 1993, February, page 33 to 34).

In the context of the invention, all distillation columns not comprising a dividing wall are referred to as conventional distillation columns. In thermally coupled conventional distillation columns, mass and energy streams are mutually exchanged. A significant saving of energy is therefore possible compared to a simple connection in series of conventional distillation columns. A connection of two thermally coupled distillation columns is preferred as an alternative to the dividing wall column. An overview of various arrangements is given, for example, in G. Kaibel et al., Chem. Ing. Tech., Vol. 61, 1989, pp. 16 to 25 and G. Kaibel et al., Gas Separation & Purification, Vol. 4, 1990, June, pp. 109 to 114.

In a first preferred embodiment, a distillation column is used for the distillation having a thermally coupled pre-column, i.e. the draw column, the upper combining column and the lower combining column take the form of a single-section distillation column, and the feed column takes the form of a pre-column to the distillation column. In a second preferred embodiment, a distillation column is used having a thermally coupled post-column, i.e. the feed column, the upper combining column and the lower combining column take the form of a single-section distillation column and the draw column takes the form of a post-column to the distillation column. Distillation columns with connected auxiliary columns are known and described, for example, in Chem. Eng. Res. Des., Part A: Trans IChemE, March 1992, pp. 118-132, "The design and optimisation of fully thermally coupled distillation columns".

It has proven to be favorable to remove at least some of the compounds with a lower boiling point than the 2-substituted 4-hydroxy-4-methyltetrahydropyrans (VI) from the reaction product from step a1) prior to introducing it into the feed column. In one specific embodiment, therefore, an arrangement of distillation columns is used for the distillative separation of the reaction product from step a), which arrangement comprises an upstream conventional distillation column and a downstream dividing wall column or a downstream interconnection of two thermally coupled conventional distillation columns.

Preferably, for the distillative separation in step a2)
a21) the reaction mixture from step a1) is firstly subjected to a separation in the conventional distillation column, wherein a first top product is obtained, which is enriched in the dioxane compound (II) and in the compounds (III.1), (III.2) and (III.3) and essentially does not comprise any compounds of the general formula (VI), and a first bottom product is obtained, which is depleted in the compounds (III.1), (III.2) and (III.3) and the dioxane compound (II) and which comprises the majority of the compounds of the general formula (VI), a22) the first bottom product from step a21) is subjected to a separation in the dividing wall column or in the two interconnected thermally coupled conventional distillation columns, wherein a second top product is obtained which comprises the compounds (III.1), (III.2), (III.3) and (II) not present in the first top product and also optionally low amounts of the compounds of the general formula (VI), and a sidestream is obtained essentially containing compound of the general formula (VI), and a second bottom product is obtained comprising the compounds of the general formula (VI) which are not present in the top product and not in the sidestream, wherein the first top product and/or the second top product are used as starting material in step b).

In the compounds of the formulae (II), (III.1), (III.2), (III.3) and (VI) in the aforementioned embodiment, $R^1$ is also preferably Isobutyl.

The expression according to which the first top product essentially does not comprise any compounds of the general formula (VI) means that the proportion of compounds of the general formula (VI) in the first top product is at most 5% by weight, particularly preferably at most 2% by weight, particularly at most 1% by weight, especially at most 0.1% by weight, based on the total weight of the first top product. In a specific embodiment, the first top product does not comprise any compounds of the general formula (VI).

The second top product may comprise, for example, 1 to 40% by weight, particularly preferably 2 to 30% by weight, particularly 5 to 25% by weight, especially 10 to 20% by weight, of compounds of the general formula (VI), based on the total weight of the second top product.

In a specific embodiment, the sidestream consists only of compounds of the general formula (VI).

Alternatively, the second bottom product may comprise compounds which have a higher boiling point than the compounds of the general formula (VI).

According to this embodiment, the first top product (particularly the organic phase of the first top product, depleted in water) and/or the second top product is preferably used for the reaction in step b) in the presence of a strong acid and/or of an acidic ion exchanger. It is not critical if the second top product still comprises low amounts of the compounds of the general formula (VI) since these pass through the reaction in step b) virtually unchanged and subsequently if desired can be separated off and utilized.

Generally in this embodiment, the side product and the second bottom product will differ with respect to the proportion of the stereoisomers of the compounds of the formula (VI).

Step b)

In step b) of the method according to the invention, the starting material provided in step a) is subjected to a reaction in the presence of a strong acid and/or an acidic ion exchanger, wherein a product mixture is obtained depleted in the dioxane compound of the formula (II) and enriched in at least one of the compounds of the formulae (III.1), (III.2) or (III.3) and also in the compound (VI), compared to the starting material,

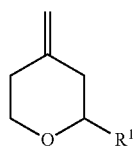
(III.1)

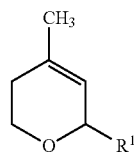
(III.2)

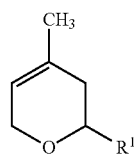
(III.3)

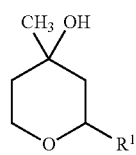
(VI)

where $R^1$ is as defined above.

Suitable acids for the reaction in step b) are in principle the acidic catalysts mentioned in step a1). The suitable and preferred embodiments of these acidic catalysts are hereby fully incorporated by reference.

In principle, any substance can be used for the reaction in step b) having Brönstedt or Lewis acidity. Examples of suitable catalysts are protic acids, acidic molecular elemental compounds, acidic ion exchangers and mixtures thereof.

The reaction in step b) is preferably carried out in the presence of an acid selected from hydrochloric acid, sulfuric acid, methanesulfonic acid, p-toluenesulfonic acid and strongly acidic cation exchangers.

In a specific embodiment, the reaction in step b) is carried out in the presence of a strongly acidic cation exchanger or methanesulfonic acid.

In a first version, the reaction in step b) takes place in the presence of a Brönstedt acid preferably selected from hydrochloric acid, sulfuric acid, methanesulfonic acid, p-toluenesulfonic acid.

In this first version, the water content of the reaction mixture is 0 to 10% by weight, particularly preferably 1 to 5% by weight, based on the total weight of the reaction mixture.

In this first version, the Brönstedt acid is preferably used in an amount of 1 to 5 mol %, particularly preferably 1 to 3 mol % of acid groups of the Brönstedt acid, based on the dioxane compound of the general formula (II).

In this first version, a solvent is optionally used in step b) preferably selected from hydrocarbons and hydrocarbon mixtures. Suitable solvents are, for example, hexane, heptane, naphtha, petroleum ether, cyclohexane, decalin, toluene, xylene and mixtures thereof. Solvent is preferably not used.

The reaction is preferably effected in step b) according to this first version at a temperature in the range of 20 to 180° C., particularly preferably 50 to 140° C.

In a second version, the reaction in step b) is effected in the presence of a strongly acidic cation exchanger. Suitable strongly acidic cation exchangers are described above in step a1), which is hereby fully incorporated by reference.

The strongly acidic ion exchange resins are generally regenerated using hydrochloric acid and/or sulfuric acid.

The reaction in step b) preferably takes place in the presence of a strongly acidic cation exchanger and in the presence of water. The reaction in step b) is then typically carried out in the presence of 1 to 10% by weight of water, particularly preferably 2 to 5% by weight of water, based on the total weight of the reaction mixture.

The amount of strongly acidic cation exchanger in step b) is not critical and may be freely selected over a wide range taking into account the economic and process technology aspects. The reaction may accordingly be carried out either in the presence of catalytic amounts or in the presence of large excesses of the strongly acidic cation exchanger. The strongly acidic cation exchanger is typically used in an amount of about 0.1 to about 5% by weight, preferably in an amount of about 0.5 to about 3% by weight and particularly preferably in an amount of about 1 to about 3% by weight, based in each case on the total weight of the reaction mixture. The figures here refer to the ready-to-use cation exchanger which is generally pretreated with water and may accordingly comprise amounts of up to about 70% by weight, preferably about 30 to about 65% by weight and particularly preferably about 40 to about 65% by weight of water. Particularly in batchwise method procedures, addition of excess amounts of water are superfluous when carrying out the method according to the invention. The strongly acidic cation exchangers mentioned may be used both individually and in the form of mixtures in step b).

The reaction in the presence of a strongly acidic cation exchanger in step b) may optionally also be carried out additionally in the presence of a solvent inert under the reaction conditions. Suitable solvents are, for example, tert-butyl methyl ether, cyclohexane, decalin, hexane, heptane, naphtha, petroleum ether, toluene or xylene. Said solvents can be used alone or in the form of mixtures with one another. The reaction in step a) is preferably carried out in the presence of a strongly acidic cation exchanger without addition of an organic solvent.

The reaction in step b) of the starting material provided in step a) is preferably carried out in the presence of water and in the presence of a strongly acidic cation exchanger at a temperature in the range of 10 to 200° C., particularly preferably at a temperature in the range of 50 to 180° C. and particularly at a temperature in the range of 80 to 150° C.

The reaction is step b) can be carried out in batchwise mode or continuously. In the batchwise case, for example, the reaction may be conducted such that the starting material provided in step a), optionally water and optionally an organic solvent is charged in a suitable reaction vessel and the acidic catalyst is added. After completion of the reaction, the strong acid can be removed from the reaction mixture obtained by suitable separation methods.

If a Brönstedt acid is used in step b), preferably selected from hydrochloric acid, sulfuric acid, methanesulfonic acid, p-toluenesulfonic acid, the acid can be removed by distillation, for example, directly or after aqueous work-up.

If a strongly acidic cation exchanger is used in step b), it can be removed, for example, by filtration or by centrifugation.

In a suitable embodiment, the reaction is carried out continuously in step b). For this purpose, a mixture of the starting material provided in step a), for example, may be prepared with water and this mixture can be brought into contact continuously with a strongly acidic cation exchanger. For instance, the selected cation exchanger may be introduced into a suitable flow reactor, for example, a stirred reactor with inlet and outlet or a tubular reactor and the starting material and the water may be continuously supplied thereto and the reaction mixture may be continuously discharged. Here, the starting materials and the water may optionally be introduced into the flow reactor as individual components or also in the form of a mixture as previously described.

The reaction in step b) is generally continued until the content of the dioxane compound of the general formula (II) in the reaction mixture is below the desired maximum value.

The reaction mixture obtained in step b) preferably comprises the dioxane compound of the formula (II) in a total amount of at most 5% by weight, particularly preferably at most 2% by weight, particularly at most 1% by weight, based on the total weight of the reaction mixture.

Preferably 5 to 50% by weight, particularly preferably 10 to 40% by weight, particularly 15 to 30% by weight of the dioxane compound of the formula (II) present in the starting material are converted into compounds of the formulae (III.1), (III.2) and (III.3) by the reaction in step b).

The reaction mixture obtained in step b) preferably comprises the compounds of the formulae (III.1), (III.2) and (III.3) in a total amount of 20 to 80% by weight, particularly preferably 35 to 65% by weight, based on the total weight of the reaction mixture.

Preferably 10 to 70% by weight, particularly preferably 20 to 60% by weight, particularly 30 to 50% by weight of the dioxane compound of the formula (II) present in the starting material are converted into the 2-substituted 4-hydroxy-4-methyltetrahydropyran of the formula (VI) by the reaction in step b).

The reaction mixture obtained in step b) preferably comprises the 2-substituted 4-hydroxy-4-methyltetrahydropyran of the formula (VI) in a total amount of 10 to 40% by weight, particularly preferably 15 to 30% by weight, based on the total weight of the reaction mixture.

In a typical composition, the reaction mixture obtained in step b) comprises the following compounds, based in each case on the total weight of the reaction mixture:
Isovaleraldehyde: 0-15% by weight,
Isoprenol: 0-5% by weight,
Dioxane compound Op: 0-2% by weight,
Compounds of the formulae (III.1), (III.2) and/or (III.3): in total 30-75% by weight,
Acetals other than (II): 0-2% by weight,
Compounds of the formula (VI): 10-35% by weight.

Step c)

In step c) of the method according to the invention, the product mixture obtained in step b) is subjected to a hydrogenation. The hydrogenation in step c) converts the compounds (III.1), (III.2) and (III.3) into the corresponding 2-substituted 4-methyltetrahydropyrans of the general formula (I).

The hydrogenation in step c) may be carried out in a conventional manner using hydrogenation catalysts of the prior art. The hydrogenation may be carried out catalytically either in the gas phase or in the liquid phase. The hydrogenation in step c) of the method according to the invention is preferably carried out in the liquid phase in the presence of a heterogeneous hydrogenation catalyst and a gas containing hydrogen.

Suitable hydrogenation catalysts include, in principle, all homogeneous and heterogeneous catalysts suitable for hydrogenating unsaturated organic compounds. These include, e.g. metals, metal oxides, metal compounds or mixtures thereof. Suitable hydrogenation catalysts preferably comprise at least one transition metal, preferably from the transition groups I and VI to VIII of the Periodic Table of the Elements. These preferably include Cu, Cr, Mo, Mn, Re, W, Fe, Rh, Co, Ni, Pd, Pt, Ru, Zn or mixtures thereof.

The catalysts may consist solely of active components, or the active components may be applied to supports. Suitable support materials are e.g. $Al_2O_3$, $SiO_2$, $ZrO_2$, $TiO_2$, activated carbon, ZnO, BaO and MgO or mixtures thereof.

To increase the catalytic activity, Fe, Co and preferably Ni may be used, including in the form of Raney catalysts or in the form of metal sponge with a very large surface area.

Raney nickel or Raney cobalt is preferably used for the hydrogenation in step c) of the method according to the invention. Furthermore, palladium on carbon or platinum on carbon may be used to advantage.

Other suitable catalysts comprise e.g. 80 to 100% by weight of nickel and/or cobalt and up to 20% by weight of activating metals such as copper and/or chromium. Such catalysts are particularly advantageously used as supported catalysts. The content of catalytically active metals of such supported catalysts is generally 5 to 80% by weight, based on the sum of catalytically active metals and supports.

The catalysts for the hydrogenation in step c) may be used as shaped bodies. Examples comprise catalyst extrudates such as ribbed extrudates and other extrudate forms, egg-shell catalysts, tablets, rings, spheres, spall, etc.

Preference is given to performing the hydrogenation in step c) at a temperature of 20 to 220° C., preferably at 40 to 200° C., particularly at 50 to 180° C.

If the reaction is carried out in the gas phase, the pressure is preferably within a range from 1 to 200 bar, particularly preferably 10 to 150 bar.

If the reaction is carried out in the liquid phase, the pressure is preferably within a range from 2 to 500 bar, particularly preferably 3 to 300 bar, particularly 4 to 250 bar, especially 5 to 200 bar.

The hydrogenation in step c) can be carried out in one reactor or in a plurality of reactors connected in series. The hydrogenation can be effected continuously or batchwise. For the batchwise hydrogenation a pressure vessel, for example, may be used. Suitable pressure vessels are, for example, autoclaves equipped with an apparatus for heating and for stirring the reactor contents. The hydrogenation is preferably carried out in the liquid phase over a fixed bed, preferably in liquid phase mode or trickle mode or in the form of a suspension catalysis.

The hydrogenation can be carried out with or without addition of a solvent. Useful solvents include alcohols, ethers, hydrocarbons such as methanol, ethanol, isopropanol, dioxane, tetrahydrofuran, n-pentane, hexane, cyclohexane, toluene, etc. The hydrogenation in step c) is preferably carried out without addition of a solvent.

For the hydrogenation in step c), the product mixture obtained in step b) can be brought into contact with a hydrogen-containing gas and a hydrogenation catalyst. Suitable hydrogen-containing gases are selected from hydrogen and mixtures of hydrogen with at least one inert gas. Suitable inert gases are, for example, nitrogen or argon. For the hydrogenation in step c), hydrogen is preferably used in undiluted form, typically at a purity of about 99.9% by volume.

The compounds (III.1), (III.2) and (III.3) present in the starting mixture are converted to 2-substituted 4-methyltetrahydropyrans (I) by the hydrogenation in step c). The starting mixture used for the hydrogenation preferably comprises compounds of the formula (III.1), (III.2) and (III.3), where the residue $R^1$ is isobutyl. The compounds (III.1), (III.2) and (III.3) present in the starting mixture are then converted to 2-isobutyl-4-methyltetrahydropyran (1) (dihydrorose oxide) by the hydrogenation in step c).

Such mixtures are suitable to a particular degree, on account of their particular odor properties, for use as aroma chemicals, for example, as components with rose-scented character for preparing fragrance compositions.

According to one specific embodiment of the method according to the invention, steps b) and c) are carried out at least partly simultaneously. For this purpose it is possible, for example, to adopt a procedure in which the reaction is carried out under the conditions of step b) until the amount of the dioxane compound of the general formula (II) in the reaction mixture is below the target maximum value, and the reaction mixture is subjected to hydrogen, a hydrogenation catalyst is optionally added, and the reaction is continued under hydrogenation conditions.

According to a further specific embodiment of the method according to the invention, steps b) and c) are carried out simultaneously, with the reaction mixture being subjected to hydrogen from the start.

Step d)

The hydrogenation product obtained in step c) is advantageously characterized by a significantly reduced content of the dioxane compound of the general formula (II) compared to the starting material. It can be converted into a form suitable for commercial use by simple purification steps.

If desired, the hydrogenation product obtained in step c) may be subjected to a further work-up. For this purpose, the hydrogenation product obtained in step c) can, in principle, be subjected to customary purification processes known to those skilled in the art. This includes, for example, a distillation, an extraction or a combination thereof.

A fraction enriched in 2-substituted 4-methyltetrahydropyrans (I) and a fraction depleted in 2-substituted 4-methyltetrahydropyrans (I) are preferably isolated from the hydrogenation product obtained in step c). The fraction depleted in 2-substituted 4-methyltetrahydropyrans (I) is preferably enriched in the dioxane compound (II) and/or the 2-substituted 4-hydroxy-4-methyltetrahydropyran of the general formula (VI).

The hydrogenation product obtained in step c) is preferably subjected to a distillative separation. Suitable apparatuses for distillative separation comprise distillation columns such as tray columns, which may be equipped with bubble-caps, sieve plates, sieve trays, structured packings, random packings, valves, side draws, etc., evaporators such as thin film evaporators, falling film evaporators, forced circulation evaporators, Sambay evaporators etc., and combinations thereof.

The hydrogenation product obtained in step c) is preferably subjected in step d) to a distillative separation in at least one distillation column which is provided with separating internals.

A fraction enriched in 2-substituted 4-methyltetrahydropyrans (I) is preferably isolated in step d) from the hydrogenation product obtained in step c), where the diastereoisomeric ratio of the cis-diastereoisomer to the trans-diastereoisomer is in a range from 60 to 40 to 100 to 0, preferably from 65 to 35 to 90 to 10.

A fraction enriched in 2-isobutyl-4-methyltetrahydropyran (I) is particularly preferably isolated in step d) from the hydrogenation product obtained in step c), where the diastereoisomeric ratio of the cis-diastereoisomer to the trans-diastereoisomer is in a range from 60 to 40 to 100 to 0, preferably from 65 to 35 to 90 to 10.

A fraction enriched in 2-substituted 4-methyltetrahydropyrans (I) is preferably isolated in step d) from the hydrogenation product obtained in step c), which fraction has a content of dioxane compounds of the general formula (II), where $R^1$ is as defined previously and is, in particular, isobutyl, of at most 2% by weight, particularly preferably at most 1% by weight, particularly preferably at most 0.1% by weight.

To remove further water-soluble impurities, the fraction enriched in 2-substituted 4-methyltetrahydropyrans (I) obtained in step d) may be subjected to at least one wash step with water. Alternatively or in addition, the fraction enriched in 2-substituted 4-methyltetrahydropyrans (I) obtained in step d) may be subjected to a further distillative purification.

The compositions according to the invention and the compositions obtainable by the method according to the invention are particularly advantageously suitable as fragrances or for providing a fragrance.

The compositions according to the invention for use as fragrances can be diluted, as desired, with at least one customary solvent in this area of application. Examples of suitable solvents are: ethanol, dipropylene glycol or ethers thereof, phthalates, propylene glycols, or carbonates of diols, preferably ethanol. Water is also suitable as solvent for diluting the fragrance compositions according to the invention and can advantageously be used together with suitable emulsifiers.

On account of the structural and chemical similarity of the components, the fragrances obtained by the method according to the invention have high stability and durability. The isomeric mixtures of 2-(2-methylpropyl)-4-methyltetrahydropyran of the formula (Ia) (dihydrorose oxide) obtainable by the method according to the invention are characterized by a pleasant rose-like character. The isomeric mixtures of 2-(2-methylpropyl)-4-hydroxy-4-methyltetrahydropyran of the formula (VIa) optionally additionally obtainable by the method according to the invention are characterized by a pleasant odor of lily of the valley.

The fragrances obtained by the method according to the invention are suitable for incorporation in cosmetic compositions and also utility and consumer goods or agents such as are described in more detail below, in which the fragrance may be incorporated in the goods mentioned or also may be applied to such goods. Here, for the purposes of the overall present invention, an organoleptically effective amount is to be understood as meaning particularly an amount which suffices, when used as intended, to bring about a scent impression for the user or consumer.

Suitable cosmetic compositions are all customary cosmetic compositions. The compositions in question are preferably perfume, Eau de Toilette, deodorants, soap, shower gel, bathing gel, creams, lotions, sunscreen, compositions for cleansing and care of hair such as shampoo, conditioner, hair gel, hair setting compositions in the form of liquids or foams and other cleansing or care compositions for the hair, compositions for decorative application on the human body, such as cosmetic sticks, for example lipsticks, lip care sticks, concealing sticks (concealers), blushers, eye shadow pencils, lip liner pencils, eyeliner pencils, eyebrow pencils, correction pencils, sunscreen sticks, antiacne sticks and comparable products, and also nail varnishes and other products for nail care.

The fragrances obtained by the method according to the invention are specifically suitable for use in perfumes, e.g. as Eau de Toilette, shower gels, bathing gels and body deodorants.

They are also suitable for aromatizing consumer or utility goods into which they are incorporated or onto which they are applied and to which they thereby impart a pleasant fresh green accent. Examples of consumer or utility goods are: room air deodorants (air care), cleaning compositions or care compositions for textiles (specifically detergents, fabric softeners), textile treatment compositions such as ironing aids, scouring agents, cleaning compositions, care compositions for treating surfaces, for example furniture, floors, kitchen appliances, glass panes and windows and also monitors, bleaches, toilet blocks, limescale removers, fertilizers, construction materials, mold removers, disinfectants, products for the car and vehicle care and the like.

The examples which follow serve to illustrate the invention, but without restricting it in any way.

EXAMPLES

Gas chromatographic analyses were carried out in accordance with the following method:
Column: DB WAX 30 m×0.32 mm;
FD 0.25 µm;
Injector temperature: 200° C.; detector temperature 280° C.;
Temperature program: Starting temp.: 50° C., at 3° C./min to 170° C.,
at 20° C./min to 230° C., 7 min isotherm;
Retention times: Isovaleraldehyde $t_R$=3.7 min
cis-Dihydrorose oxide $t_R$=8.4 min
trans-Dihydrorose oxide $t_R$=9.6 min
4,4-Dimethyl-2-isobutyl-1,3-dioxane $t_R$=11.9 min
Concentrations of the resulting crude products (% by weight) were determined by GC analysis using an internal standard.

Example 1

(Reaction of 4,4-Dimethyl-2-Isobutyl-1,3-Dioxane with an Acidic Ion Exchanger)

4,4-Dimethyl-2-isobutyl-1,3-dioxane (30 g, purity>99%) was charged and treated with the acidic ion exchanger Amberlyst 131H wet (6 g, 20% by weight, based on 4,4-dimethyl-2-isobutyl-1,3-dioxane) and the mixture was heated (86 to 92° C.) under reflux with stirring. After a reaction time of 20 h, a crude product was obtained with the following composition: isovaleraldehyde: 14.9 GC % by weight ($t_R$=3.6 min); dihydropyrans (III.1-III.3): 15.2 GC % by weight ($t_R$=9.4, 11.0, 11.5 min); isoprenol: 0.7 GC % by weight ($t_R$=9.7 min); 4,4-dimethyl-2-isobutyl-1,3-dioxane: 13.8 GC % by weight ($t_R$=11.3 min); 2-isobutyl-4-hydroxy-4-methyltetrahydropyran: 35.4 GC % by weight ($t_R$=27.2, 28.6 min).

Example 2

(Reaction of the Low Boilers Isolated in a Dividing Wall Column in the Separation of a Reaction Mixture from the Reaction of Isovaleraldehyde and Isoprenol):

A mixture (total=2000 g) of isovaleraldehyde (0.5%), isoprenol (7.7%), the isomeric dihydropyrans of the formulae (III.1), (III.2) and (III.3) (43.5%), 4,4-dimethyl-2-isobutyl-1,3-dioxane (29.7%) and 2-isobutyl-4-hydroxy-4-methyltetrahydropyran (17.1%) was charged in an autoclave (max. filling 3500 ml) and treated with Amberlyst 131H wet (40 g, 2% by weight, based on the reaction mixture used). After closing, the autoclave was heated to 120° C. and stirred for 10 h at this temperature. After cooling to room temperature, the output was filtered through a suction filter (nominal diameter of the pores 10 to 16 µm). The crude product was obtained with the following composition: isovaleraldehyde: 7.0 GC % by weight ($t_R$=3.6 min); dihydropyrans (III.1-III.3): 51.2 GC % by weight ($t_R$=9.3, 11.1, 11.6 min); isoprenol: 0.3 GC % by weight ($t_R$=9.9 min);

4,4-dimethyl-2-isobutyl-1,3-dioxane: 0.7 GC % by weight ($t_R$=11.3 min); 2-isobutyl-4-hydroxy-4-methyltetrahydropyran: 21.2 GC % by weight ($t_R$=27.2 min, 28.5 min).

Example 3

(Hydrogenation of the Output from the Acidic Reaction in Example 2)

A mixture (total=1700 g) of isovaleraldehyde (7.0%), the isomeric dihydropyrans of the formulae (III.1), (III.2) and (III.3) (51.2%), isoprenol (0.3%), 4,4-dimethyl-2-isobutyl-1,3-dioxane (0.7%) and pyranol (21.2%) was charged in an autoclave (max. filling 3500 ml) and treated with Raney nickel catalyst (water-moist; 18 g). After closing, the autoclave was flushed three times with nitrogen (20 bar), the stirrer was engaged (700 rpm), hydrogen was injected to a pressure of 10 bar, and the autoclave was heated to 150° C. At 150° C., 70 bar of hydrogen were injected and the batch was stirred under this pressure for a further 6 h. After cooling to room temperature and being let down to 0 bar, the output was filtered through a suction filter (nominal diameter of the pores 10 to 16 μm). The crude product was obtained with the following composition: isovaleraldehyde: 1.2 GC % by weight (tR=3.7 min); cis-dihydrorose oxide: 23.1 GC % by weight (tR=7.9 min); isoamyl alcohol: 6.7 GC % by weight (tR=8.6 min); trans-dihydrorose oxide: 25.3 GC % by weight (tR=9.1 min); 4,4-dimethyl-2-isobutyl-1,3-dioxane: 1.1 GC % by weight (tR=11.2 min); 2-isobutyl-4-hydroxy-4-methyl-tetrahydropyran: 21.0 GC % by weight (tR=27.2, 28.5 min).

Example 4

(Reaction of the Low Boilers Isolated in a Dividing Wall Column in the Separation of a Reaction Mixture from the Reaction of Isovaleraldehyde and Isoprenol):

A mixture (total=100 g) of isovaleraldehyde (0.4%), isoprenol (0.3%), the isomeric dihydropyrans of the formulae (III.1), (III.2) and (III.3) (67.8%), 4,4-dimethyl-2-isobutyl-1,3-dioxane (18.2%) and 2-isobutyl-4-hydroxy-4-methyltetrahydropyran (13.0%) was charged in an autoclave (max. filling 300 ml) and treated with Amberlyst 131H wet (1 g, 1% by weight, based on the reaction mixture used). After closing, the autoclave was heated to 130° C. and stirred for 10 h at this temperature. After cooling to room temperature, the output was filtered through a suction filter (nominal diameter of the pores 10 to 16 μm). The crude product was obtained with the following composition: isovaleraldehyde: 3.1 GC % by weight (tR=3.6 min); dihydropyrans (III.1-III.3): 66.3 GC % by weight ($t_R$=9.4, 11.2, 11.7 min); isoprenol: 0.4 GC % by weight ($t_R$=9.9 min); 4,4-dimethyl-2-isobutyl-1,3-dioxane: 0.1 GC % by weight ($t_R$=11.4 min); 2-isobutyl-4-hydroxy-4-methyltetrahydropyran: 11.6 GC % by weight ($t_R$=27.2 min, 28.6 min).

Example 5

(Hydrogenation of the Output from the Acidic Reaction in Example 4)

A mixture (total=60 g) of isovaleraldehyde (3.1%), the isomeric dihydropyrans of the formulae (III.1), (III.2) and (III.3) (66.3%), isoprenol (0.4%), 4,4-dimethyl-2-isobutyl-1,3-dioxane (0.1%) and 2-isobutyl-4-hydroxy-4-methyltetrahydropyran (11.6%) was charged in an autoclave (max. filling 300 ml) and treated with Raney nickel catalyst (water-moist; 0.6 g). After closing, the autoclave was flushed three times with nitrogen (20 bar), the stirrer was engaged (700 rpm), hydrogen was injected to a pressure of 10 bar, and the autoclave was heated to 150° C. At 150° C., 70 bar of hydrogen were injected and the batch was stirred under this pressure for a further 10 h. After cooling to room temperature and being let down to 0 bar, the output was filtered through a suction filter (nominal diameter of the pores 10 to 16 μm). The crude product was obtained with the following composition: cis-dihydrorose oxide: 33.9 GC % by weight (tR=7.9 min); isoamyl alcohol: 2.6 GC % by weight (tR=8.6 min); trans-dihydrorose oxide: 32.6 GC % by weight (tR=9.2 min); 4,4-dimethyl-2-isobutyl-1,3-dioxane: 0.5 GC % by weight (tR=11.2 min); 2-isobutyl-4-hydroxy-4-methyl-tetrahydropyran: 11.7 GC % by weight (tR=27.2, 28.6 min).

Example 6

(Acidic Reaction and Hydrogenation in One Stage)

A mixture (total=100 g) of isovaleraldehyde (11.8%), the isomeric dihydropyrans of the formulae (III.1), (III.2) and (III.3) (48.7%), isoprenol (10.5%), 4,4-dimethyl-2-isobutyl-1,3-dioxane (20.4%) and 2-isobutyl-4-hydroxy-4-methyl-tetrahydropyran (6.0%) was charged in an autoclave (max. filling 300 ml) and treated with Amberlyst 131H wet (10 g, 10% by weight, based on the reaction mixture used) and with Raney nickel catalyst (water-moist; 1.0 g). After closing, the autoclave was flushed three times with nitrogen (20 bar), the stirrer was engaged (700 rpm), hydrogen was injected to a pressure of 10 bar, and the autoclave was heated to 130° C. At 130° C., 50 bar of hydrogen were injected and stirring took place under this pressure for a further 20 h. After cooling to room temperature and being let down to 0 bar, the output was filtered through a suction filter (nominal diameter of the pores 10 to 16 μm). The crude product was obtained with the following composition: isovaleraldehyde: 2.5 GC % by weight ($t_R$=3.7 min); cis-dihydrorose oxide: 18.8 GC % by weight (tR=7.9 min); isoamyl alcohol: 12.7 GC % by weight (tR=8.7 min); trans-dihydrorose oxide: 28.4 GC % by weight (tR=9.2 min); 4,4-dimethyl-2-isobutyl-1,3-dioxane: 0.2 GC % by weight (tR=11.3 min); 2-isobutyl-4-hydroxy-4-methyl-tetrahydropyran: 6.0 GC % by weight (tR=27.2, 28.6 min).

Example 7

(Reaction of the Low Boilers Isolated in a Dividing Wall Column in the Separation of a Reaction Mixture from the Reaction of Isovaleraldehyde and Isoprenol):

A mixture (total=60 g) of isovaleraldehyde (0.3%), isoprenol (0.3%), the isomeric dihydropyrans of the formulae (III.1), (III.2) and (III.3) (66.1%), 4,4-dimethyl-2-isobutyl-1,3-dioxane (17.8%) and 2-isobutyl-4-hydroxy-4-methyltetrahydropyran (12.7%) was treated with Amberlyst 131H wet (3 g, 5% by weight, based on the reaction mixture used). The mixture was subsequently heated to reflux and stirred for 13 h. After cooling to room temperature, the output was filtered through a suction filter (nominal diameter of the pores 10 to 16 μm). The crude product was obtained with the following composition: isovaleraldehyde: 4.5 GC % by weight ($t_R$=3.6 min); dihydropyrans (III.1-III.3): 68.8 GC % by weight (tR=9.4, 11.2, 11.7 min); isoprenol: 0.4 GC % by weight ($t_R$=9.9 min); 4,4-dimethyl-2-isobutyl-1,3-dioxane: 2.4 GC % by weight ($t_R$=11.4 min); 2-isobutyl-4-hydroxy-4-methyltetrahydropyran: 19.5 GC % by weight ($t_R$=27.3 min, 28.6 min).

The invention claimed is:

1. A method for preparing 2-substituted 4-methyltetrahydropyrans of the general formula (I)

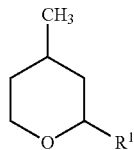
(I)

in which

R¹ is a straight-chain or branched $C_1$-$C_{12}$-alkyl, straight-chain or branched $C_2$-$C_{12}$-alkenyl, unsubstituted or $C_1$-$C_{12}$-alkyl- and/or $C_1$-$C_{12}$-alkoxy-substituted cycloalkyl having a total of 3 to 20 carbon atoms or unsubstituted or $C_1$-$C_{12}$-alkyl- and/or $C_1$-$C_{12}$-alkoxy-substituted aryl having a total of 6 to 20 carbon atoms, comprising a) providing a starting material comprising at least one dioxane compound of the general formula (II)

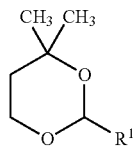
(II)

where R¹ is as defined above, b) subjecting the starting material to a reaction in the presence of a strong acid and/or an acidic ion exchanger, wherein, compared to the starting material, a product mixture depleted in the dioxane compound of the formula (II) and enriched in at least one of the compounds of the formulae (III.1), (III.2) or (III.3)

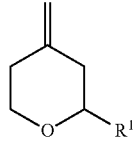
(III.1)

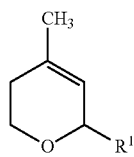
(III.2)

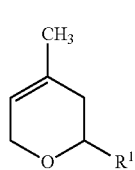
(III.3)

is obtained where R¹ is as defined above, c) subjecting the product mixture obtained in step b) to a hydrogenation.

2. The method according to claim 1, wherein a starting material is provided in step a) which additionally comprises at least one of the compounds of the formulae (III.1), (III.2) or (III.3),

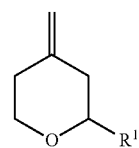
(III.1)

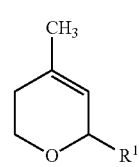
(III.2)

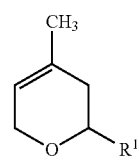
(III.3)

in which

R¹ is a straight-chain or branched $C_1$-$C_{12}$-alkyl, straight-chain or branched $C_2$-$C_{12}$-alkenyl, unsubstituted or $C_1$-$C_{12}$-alkyl- and/or $C_1$-$C_{12}$-alkoxy-substituted cycloalkyl having a total of 3 to 20 carbon atoms or unsubstituted or $C_1$-$C_{12}$-alkyl- and/or $C_1$-$C_{12}$-alkoxy-substituted aryl having a total of 6 to 20 carbon atoms.

3. The method according to claim 1, wherein, to provide the starting material in step a):

a1) 3-Methylbut-3-en-1-ol of the formula (IV)

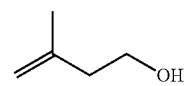
(IV)

is reacted in the presence of an acidic catalyst with an aldehyde of the formula (V)

 —CHO    (V)

in which

R¹ is a straight-chain or branched $C_1$-$C_{12}$-alkyl, straight-chain or branched $C_2$-$C_{12}$-alkenyl, unsubstituted or $C_1$-$C_{12}$-alkyl- and/or $C_1$-$C_{12}$-alkoxy-substituted cycloalkyl having a total of 3 to 20 carbon atoms or unsubstituted or $C_1$-$C_{12}$-alkyl- and/or $C_1$-$C_{12}$-alkoxy-substituted aryl having a total of 6 to 20 carbon atoms, wherein a reaction mixture is obtained comprising at least one dioxane compound (II), at least one of the compounds (111.1), (III.2) or (III.3) and at least one 2-substituted 4-hydroxy-4-methyltetrahydropyran of the general formula (VI)

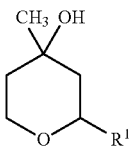

(VI)

wherein R¹ in formula (VI) is as defined above.

4. The method according to claim 3, which further comprises
a2) subjecting the reaction mixture from step a1) to a separation to obtain at least one fraction enriched in 2-substituted 4-hydroxy-4-methyltetrahydropyrans of the general formula (VI) and a fraction comprising the dioxane compound (II) and at least one of the compounds (III.1), (III.2) or (III.3), and the reaction product obtained in step a1), or the fraction which is obtained in step a2) and which comprises the dioxane compound (II) and at least one of the compounds (III.1), (III.2) or (III.3), is used as starting material for preparing the 2-substituted 4-methyltetrahydropyrans of the formula (I).

5. The method according to claim 4, wherein the reaction product from step a1) is subjected to a distillative separation in step a2).

6. The method according to claim 5, wherein in step a2), an arrangement of distillation columns is used for the distillative separation of the reaction product from step a1), which arrangement comprises an upstream conventional distillation column and a downstream dividing wall column or a downstream interconnection of two thermally coupled conventional distillation columns, and
a21) the reaction mixture from step a1) is firstly subjected to a separation in the conventional distillation column, wherein a first top product is obtained, which is enriched in the dioxane compound (II) and in the compounds (III.1), (III.2) and (III.3) and essentially does not comprise any compounds of the general formula (VI), and a first bottom product is obtained, which is depleted in the compounds (III.1), (III.2) and (III.3) and the dioxane compound (II) and which comprises the majority of the compounds of the general formula (VI),
a22) the first bottom product from step a21) is subjected to a separation in the dividing wall column or in the two interconnected thermally coupled conventional distillation columns, wherein a second top product is obtained which comprises the compounds (III.1), (III.2), (III.3) and (II) not present in the first top product and also optionally low amounts of the compounds of the general formula (VI), and a sidestream is obtained essentially containing compound of the general formula (VI), and a second bottom product is obtained comprising the compounds of the general formula (VI) which are not present in the top product and not in the sidestream, wherein the first top product and/or the second top product are used as starting material in step b).

7. The method according to claim 1, wherein the residue R¹ is isobutyl or phenyl.

8. The method according to claim 3, in which the reaction in step a1) and/or in step b) is effected in the presence of an acid, selected from hydrochloric acid, sulfuric acid, methanesulfonic acid, p-toluenesulfonic acid and strongly acidic cation exchangers.

9. The method according to claim 8, in which the reaction in step a1) and/or in step b) is carried out in the presence of a strongly acidic cation exchanger.

10. The method according to claim 1, wherein steps b) and c) are carried out at least partly simultaneously.

11. The method according to claim 1, wherein the hydrogenation in step c) is effected in the presence of a hydrogenation catalyst, selected from homogeneous and heterogeneous catalysts comprising at least one metal component, selected from metals, metal oxides, metal compounds or mixtures thereof.

12. The method according to claim 1, wherein the hydrogenation in step c) is effected in the presence of a hydrogenation catalyst, selected from palladium on carbon, platinum on carbon, Raney nickel or Raney cobalt.

13. The method according to claim 1, wherein the hydrogenation product obtained in step c) is subjected to a distillative separation step d).

14. The method according to claim 13, wherein a fraction enriched in 2-substituted 4-methyltetrahydropyrans (I) is isolated in step d) from the hydrogenation product obtained in step c), said fraction comprising dioxane compounds of the general formula (II) of not more than 2% by weight.

15. The method according to claim 13, wherein a fraction enriched in 2-substituted 4-methyltetrahydropyrans (I) is isolated in step d) from the hydrogenation product obtained in step c), said fraction comprising dioxane compounds of the general formula (II) of not more than 1% by weight.

16. The method according to claim 13, wherein a fraction enriched in 2-substituted 4 methyltetrahydropyrans (I) is isolated in step d) from the hydrogenation product obtained in step c), said fraction comprising dioxane compounds of the general formula (II) of not more than 0.5% by weight.

17. The method according to claim 13, wherein a fraction enriched in 2-substituted 4-methyltetrahydropyrans (I) is isolated in step d) from the hydrogenation product obtained in step c), said fraction comprising dioxane compounds of the general formula (II) of not more than 0.1% by weight.

18. The method according to claim 13, wherein the fraction obtained in step d) and enriched in 2-substituted 4-methyltetrahydropyrans (I) is subjected to at least one washing step with water and/or to a further distillative purification.

19. The method according to claim 1 for preparing 2-isopropyl-4-methyltetrahydropyran (I).

* * * * *